US011200674B2

(12) United States Patent
Emoto et al.

(10) Patent No.: US 11,200,674 B2
(45) Date of Patent: Dec. 14, 2021

(54) IMAGE PROCESSING APPARATUS, METHOD, AND STORAGE MEDIUM FOR ENABLING USER TO REC0GNT7E CHANGE OVER TIME REPRESENTED BY SUBSTRACTION IMAGE

(71) Applicant: CANON KABUSHIKI KAISHA, Tokyo (JP)

(72) Inventors: Yutaka Emoto, Kyoto (JP); Yoshio Iizuka, Kawasaki (JP); Masahiro Yakami, Kyoto (JP); Mizuho Nishio, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/656,451

(22) Filed: Oct. 17, 2019

(65) Prior Publication Data

US 2020/0134823 A1    Apr. 30, 2020

(30) Foreign Application Priority Data

Oct. 29, 2018  (JP) .............................. JP2018-202866

(51) Int. Cl.
*G06T 7/00* (2017.01)
*G06T 5/50* (2006.01)
*G09G 5/14* (2006.01)
*G16H 30/20* (2018.01)
*G16H 30/40* (2018.01)
*G06T 5/00* (2006.01)

(52) U.S. Cl.
CPC ............ *G06T 7/0016* (2013.01); *G06T 5/002* (2013.01); *G06T 5/50* (2013.01); *G09G 5/14* (2013.01); *G16H 30/20* (2018.01); *G16H 30/40* (2018.01); *G06T 2207/10081* (2013.01); *G06T 2207/10088* (2013.01); *G06T 2207/20224* (2013.01); *G06T 2207/30008* (2013.01); *G06T 2207/30016* (2013.01); *G06T 2207/30056* (2013.01); *G06T 2207/30061* (2013.01); *G09G 2340/12* (2013.01); *G09G 2380/08* (2013.01)

(58) Field of Classification Search
CPC ................................................... G06T 7/0016
USPC ......................................................... 345/611
See application file for complete search history.

(56) References Cited

U.S. PATENT DOCUMENTS

2008/0193005 A1* 8/2008 Seghers .................. G06T 7/254
                                                              382/131
2017/0301080 A1* 10/2017 Yan ........................ G06T 7/0016
2020/0082931 A1* 3/2020 Nakatsugawa ...... G06K 9/6215

FOREIGN PATENT DOCUMENTS

WO       2015/029135 A1    3/2015

* cited by examiner

*Primary Examiner* — Shivang I Patel
(74) *Attorney, Agent, or Firm* — Canon U.S.A., Inc. IP Division

(57) ABSTRACT

An image processing apparatus supports detection of pathological change over time in portion of a captured region commonly included in a first image and a second image, the first image and the second image acquired by capturing a subject at different respective times. The image processing apparatus includes an acquisition unit configured to acquire a subtraction image of the first image and the second image representing the pathological change over time as a difference and a recording unit configured to record information indicating said portion using a name different from a name of the commonly included region in a storage unit in association with the subtraction image.

15 Claims, 10 Drawing Sheets

IMAGE PROCESSING APPARATUS, METHOD, AND STORAGE MEDIUM FOR ENABLING USER TO REC0GNT7E CHANGE OVER TIME REPRESENTED BY SUBSTRACTION IMAGE

BACKGROUND

Field

Disclosure of this specification relates to an image processing apparatus, an image processing method, and a storage medium.

Description of the Related Art

An image subtraction technique to support a user to make a comparison between images is known in medical field (WO2015/029135). In this technique, registration adjustment is performed between two images captured at different times, and a subtraction image that visualizes a difference between the images is displayed.

SUMMARY

It has now been determined that in a conventional subtraction image, although a portion having pathological change over time is visualized clearly, a portion without having pathological change over time is visualized unclearly, and accordingly, there is a case where the user finds it difficult to recognize what sort of pathological change over time the subtraction image represents.

According to an aspect of the present disclosure, a user is enabled to recognize what sort of pathological change over time the subtraction image represents.

According to another aspect of the present disclosure, advantageous functions and effects can be derived from respective configurations and embodiments of the present disclosure such as ones detailed in the below-described exemplary embodiments of the present disclosure, which advantageous functions and effects cannot be acquired from conventional techniques.

According to another aspect of the present disclosure, an image processing apparatus supports detection of pathological change over time in a portion of a captured region, the captured region being common to a first image and a second image, the first image and the second image acquired by capturing a subject at different times. The image processing apparatus includes an acquisition unit configured to acquire a subtraction image of the first image and the second image representing the pathological change over time as a difference and a recording unit configured to record information indicating said portion using a name different from a name of the commonly included region in a storage unit in association with the subtraction image.

According to another aspect of the present disclosure, it can be possible to recognize what sort of pathological change over time a subtraction image represents.

Further features of the present disclosure will become apparent from the following description of exemplary embodiments (with reference to the attached drawings).

DESCRIPTION OF THE EMBODIMENTS

Figure 1:
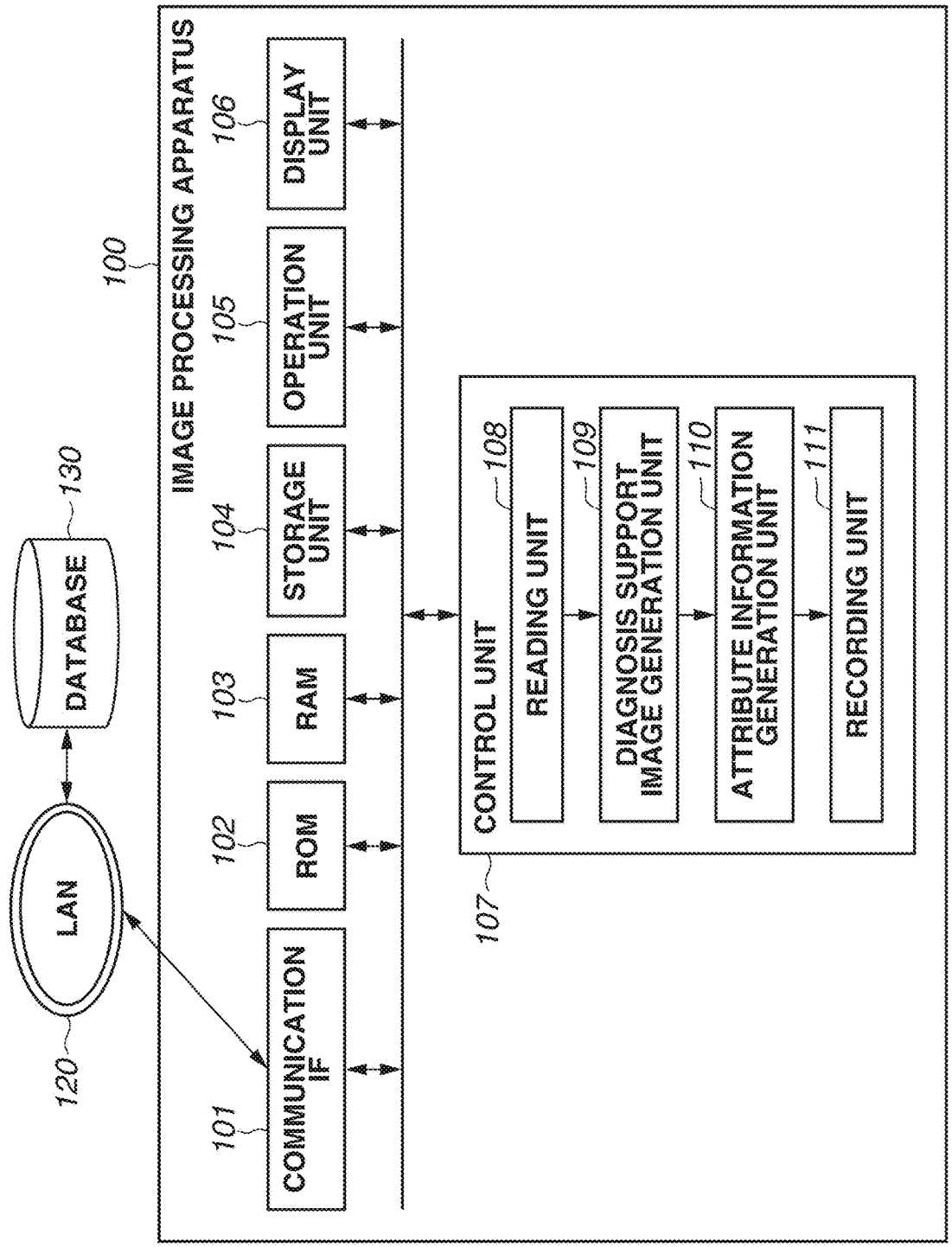
FIG. 1 is a block diagram illustrating an example of an overall configuration of an image processing system including an image processing apparatus according to a first exemplary embodiment.

Hereinafter, exemplary embodiments of an image processing apparatus according to the present disclosure will be described with reference to the appended drawings. A scope of the present disclosure is not, however, limited to the examples illustrated in the drawings.

An image processing apparatus according to a first exemplary embodiment records a diagnosis support image in association with attribute information including diagnosis support region information. The diagnosis support image is acquired from medical images acquired by capturing a subject through various types of medical image-capturing apparatuses (modalities), such as an X-ray computed tomography (CT) scanner and a magnetic resonance imaging (MRI) apparatus.

In the below-described exemplary embodiment, a medical image captured by an image-capturing apparatus, such as a CT scanner or an MRI apparatus, will be described as an "original image" in order to distinguish the medical image from the diagnosis support image. The original image and the diagnosis support image are simply described as "images" when these images are described without being distinguished from one another. In addition, the images according to the disclosure of this specification includes not only images displayed on a display unit but also images stored in a database or a storage unit as image data.

Below-described exemplary embodiments are merely examples to describe a processing method of the image processing apparatus, and disclosure of this specification is not limited to the exemplary embodiments.

FIG. 1 is a block diagram illustrating an overall configuration of an image processing system including the image processing apparatus according to the present exemplary embodiment.

The image processing system includes an image processing apparatus 100 and a database 130, which are communicably connected to each other via a communication means 120. In the present exemplary embodiment, the communication means 120 is configured of a local area network (LAN).

The database 130 stores and manages data such as a medical image. The image processing apparatus 100 acquires a medical image managed by the database 130 via the communication means (e.g., LAN) 120.

The image processing apparatus 100 includes, as a functional configuration, a communication interface (IF) 101, a read only memory (ROM) 102, a random access memory (RAM) 103, a storage unit 104, an operation unit 105, a display unit 106, and a control unit 107.

The communication IF 101 is implemented by, for example, a LAN card, and is responsible for communication executed between an external apparatus (e.g., database 130) and the image processing apparatus 100. The ROM 102 is, for example, a non-volatile memory, and stores various programs. The RAM 103 is r, for example, a volatile memory, and temporarily stores various kinds of information. The storage unit 104 is one example of a computer-readable storage medium. The storage unit 104 is, for example, a large-capacity information storage device represented by a hard disk drive (HDD) or a solid state drive (SSD), and various kinds of information are stored therein. The operation unit 105 is a keyboard or a mouse, and an instruction from a user is input to the image processing apparatus 100 through the operation unit 105. The display unit 106 is a display, and displays various kinds of information to the user. The control unit 107 is implemented by a central processing unit (CPU), and integrally controls various types of processing executed by the image processing apparatus 100.

The control unit 107 includes, as a functional configuration, a reading unit 108, a diagnosis support image generation unit 109, an attribute information generation unit 110, and a recording unit 111.

The reading unit 108 reads out an original image and records the original image in the storage unit 104. The diagnosis support image generation unit 109 generates a diagnosis support image from the original image by using a known technique. The attribute information generation unit 110 generates attribute information of the diagnosis support image by using the attribute information and the diagnosis support region information acquired from the original image data. The recording unit 111 records attribute information of a diagnosis support image and the diagnosis support image in the storage unit 104 in association with each other.

Figure 2:
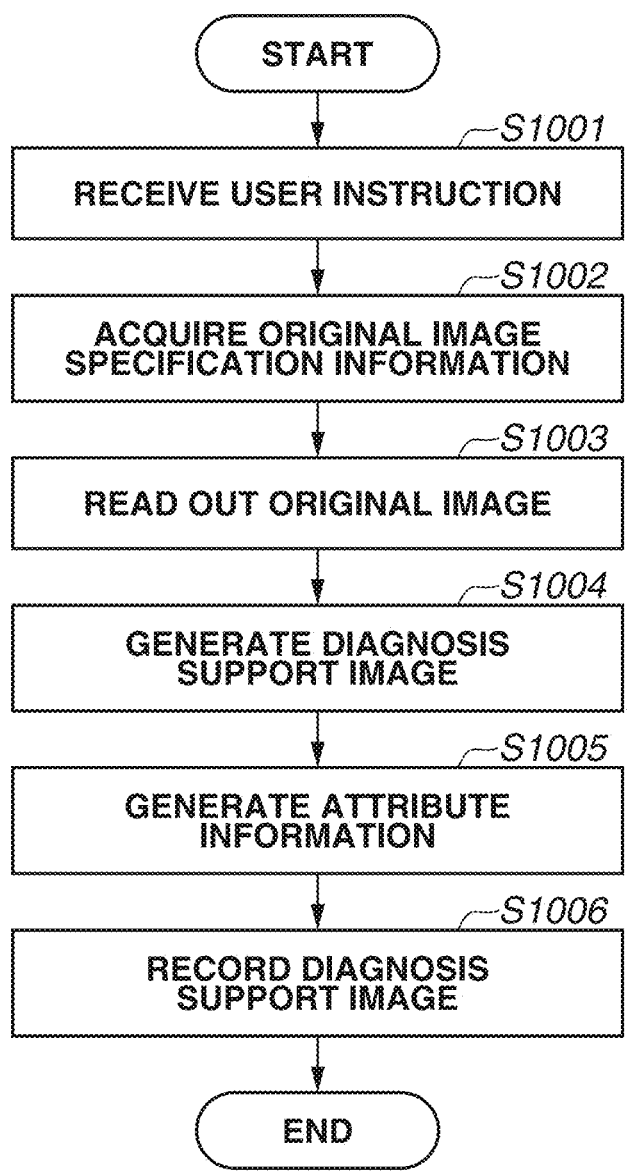
FIG. 2 is a flowchart illustrating an example of a processing procedure according to the first exemplary embodiment.

Functions of respective units included in the control unit 107 will be described in detail with reference to the flowchart in FIG. 2.

In the below-described exemplary embodiment, it is assumed that image data is saved in a format compliant with an international standard, i.e., a standard of the digital imaging and communication in medicine (DICOM), which specifies a medical image format and communication procedure. A format compliant with the DICOM standard is assumed to specifically describe attribute information of image data. However, the format does not have to be compliant with the DICOM standard as long as attribute information similar to the below-described attribute information can be saved in association with the image.

Hereinafter, an image saved in a format compliant with the DICOM standard is described as a DICOM image. Further, the above-described DICOM header generally refers to a data area in which information other than information about a pixel value of DICOM data is recorded. The DICOM header includes examination information, patient information, and image attribute information.

First, processing procedure of the image processing apparatus 100 according to the present exemplary embodiment will be described with reference to the flowchart in FIG. 2.

<Receiving User Instruction>

In step S1001, the control unit 107 receives a user instruction input from the operation unit 105. Herein, it is assumed that the control unit 107 receives, for example, an instruction for generating a diagnosis support image. Although there are a wide variety of user instructions relating to control executed by the control unit 107, description of the other user instructions will be omitted in order to simply describe the disclosure of this specification.

<Acquiring Original Image Specification Information>

In step S1002, the control unit 107 receives information (hereinafter, referred to as "original image specification information") for specifying one or more original images used for generating the diagnosis support image input to the operation unit 105. The number of original images varies depending on the type of diagnosis support image to be acquired. Hereinafter, in order to specifically describe the present exemplary embodiment, a processing procedure using a subtraction image as a diagnosis support image will be described as an example. The subtraction image is generated by calculating a difference between two original images after registration is adjusted between the two original images. Hereinafter, two CT images acquired by capturing the same subject at different times are used as the original images. The CT images are three-dimensional images and a subtraction image acquired from the two CT images is also a three-dimensional image. In other words, the subtraction image described in this specification illustrates pathological change over time between the first image and the second image acquired by capturing the subject at different times as a difference. More specifically, the subtraction image illustrates pathological change over time of a portion of a captured region as a difference. The aforementioned portion is a portion of a region commonly included in the first and the second images acquired by capturing the subject at different times, and a name used for the aforementioned portion is different from a name of the aforementioned region commonly included in the first and the second images. However, disclosure of this specification is not limited to the following exemplary embodiment, and can be applied to a case where an optional diagnosis support image acquired from the optional types and the optional number of original images is used.

<Reading Out Original Image>

In step S1003, based on the original image specification information received in step S1002, the reading unit 108 reads out original image data (e.g., two pieces of CT image data) from the database 130 via the communication IF 101 and the LAN 120, and records the original image data in the storage unit 104. An area including a common region is captured in the two pieces of original image data. At this time, if a size of the RAM 103 is large enough, the read original image data may be recorded in the RAM 103.

<Generating Diagnosis Support Image>

In step S1004, the diagnosis support image generation unit 109 acquires a diagnosis support image from the original image data recorded in the storage unit 104 (or the RAM 103) by using a known technique. In other words, the diagnosis support image generation unit 109 generates a subtraction image from the two pieces of CT image data by using a known image registration adjustment technique and a known subtraction technique. For example, in the registration adjustment processing, registration is adjusted after pixel sizes of the two original images are adjusted isotropically, so that pixels that express a region common to the two original images substantially conform to each other. The diagnosis support image generation unit 109 further acquires information (e.g., diagnosis support region information or region information) to identify a region of the patient's body where diagnosis is supported by the generated diagnosis support image. For example, a name of a region directly input by the user may be acquired as the diagnosis support region information. Alternatively, an optional name may be selected by the user from a plurality of region names displayed on the display unit 106 in a tab format. The diagnosis support region information is not limited to the name of the region, and may be a display parameter such as a window level and a window width (WL/WW) which enable the user to visually recognize a selected portion when the selected portion is emphasized. The region name and the display parameter are examples of the diagnosis support region information, and the information is not limited to the above.

The processing in step S1004 may be executed after the processing in step S1005.

<Generating Attribute Information>

In step S1005, the attribute information generation unit 110 acquires attribute information from the original image data recorded in the storage unit 104 or the RAM 103.

The attribute information generation unit 110 then generates attribution information of the diagnosis support image by using the attribute information acquired from the original image data and the diagnosis support region information acquired in step S1004. If the original images are DICOM images, attribute information of the image is written in the DICOM headers. Herein, of the two CT images (original images), the CT image captured at a later time point is specified as a diagnosis target image.

In this case, patient information, such as a patient's name, and attribute information, such as an examination region, are acquired from the DICOM headers of the DICOM image captured at a later time point. An examination date/time is acquired from each of the DICOM headers of the two CT images. The attribute information generation unit 110 uses the attribute information, which is acquired from the DICOM headers of the original images, as the attribute information of the diagnosis support image. The attribute information generation unit 110 further uses a predetermined DICOM tag to write the diagnosis support region information into the DICOM header.

For example, if the diagnosis support image is a subtraction image generated from the two CT images of a captured abdominal region, which emphasizes a difference of a bone region, the diagnosis support region information indicating "bone region" is associated with the subtraction image. This corresponds to an example of a configuration in which a name of a portion of a region associated with the diagnosis support image is different from a name of the region commonly included in the two original images associated with the original images. The above-described name is merely an example, and the captured region may be "pectoral region", "thoraco-abdominal region", or "cephalic region", and the portion of the region may be "liver", "lung field", or "brain". Alternatively, a display parameter, such as (WL/WW)=(500/2500), is associated with the diagnosis support image.

In a case where the information acquired from the DICOM header of the original image is not used as the attribute information of the diagnosis support image, information does not have to be written into a DICOM tag that is not to be used, or a certain value that does not depend on the original value may be written. For example, if the information about (WL/WW) of the original image is not used as the attribute information of the diagnosis support image, values such as "(0/800)" are written regardless of the original values. In other words, it is not necessary to maintain the attribute information of the original image.

A name or a value of the information to be associated with the diagnosis support image is one example and is not limited thereto.

<Recording Diagnosis Support Image>

In step S1006, the recording unit 111 records the diagnosis support image acquired in step S1004 in the storage unit 104 (or the RAM 103) in association with the attribute information of the diagnosis support image acquired in step S1005. If the diagnosis support image is a three-dimensional image and is also a DICOM image, each of tomographic images constituting the three-dimensional image is regarded as a DICOM (tomographic) image. In other words, each of the DICOM (tomographic) images includes a DICOM header including the attribute information of the diagnosis support image and image data corresponding to a single tomographic image of the diagnosis support image.

In step S1006, the recording unit 111 may further writes the diagnosis support image associated with the attribute information into the database 130 via the communication IF 101 and the LAN 120.

As described above, the processing of the image processing apparatus 100 is executed.

Through the above-described configuration, the attribute information of the diagnosis support image and the diagnosis support image can be recorded in association with each other, the user can easily recognize which portion of the captured region is emphasized in the diagnosis support image. As illustrated in, for example, an image display area 804 in FIG. 8, a subtraction image only emphasizes a portion with pathological change over time, it is not easy for the user to recognize a portion with the difference just by looking at the subtraction image. However, even in the above-described situation, the user can easily recognize a difference of what portion of the captured region is illustrated in the subtraction image by referring to the attribute information associated with the diagnosis support image. With the above-described configuration, data can be sorted for each of the diagnosis support regions to be noticed even in a case where a large volume of image data is stored in the database 130 or the storage unit 104.

Variation Example 1-1

In the present exemplary embodiment, the diagnosis support image is recorded in the storage unit 104 (or the RAM 103) in association with the attribute information of the diagnosis support image which is generated by the attribute information generation unit 110 after the diagnosis support image is generated from the original image data (e.g., two pieces of CT image data) by the diagnosis support image generation unit 109.

However, if the diagnosis support image is previously stored in the storage unit 104 or the database 130, the image processing apparatus 100 may acquire the diagnosis support image from the storage unit 104 or the database 130 to associate the attribute information including diagnosis support region information with the diagnosis support image.

Through the above-described configuration, with respect to the diagnosis support image already stored in the storage unit 104 or the database 130, the image processing apparatus 100 can associate the attribute information without necessity to generate the diagnosis support image from the original image again. Therefore, the diagnosis support image associated with the attribute information including the diagnosis support region information can be recorded without occupying the capacity of the database 130 or the storage unit 104.

An image processing apparatus according to a second exemplary embodiment is an apparatus displaying a plurality of images, capable of setting or changing one or more display modes of the images.

An exemplary embodiment described below is merely an example for describing a processing method of the image processing apparatus, and thus disclosure of this specification is not limited thereto.

Figure 3:
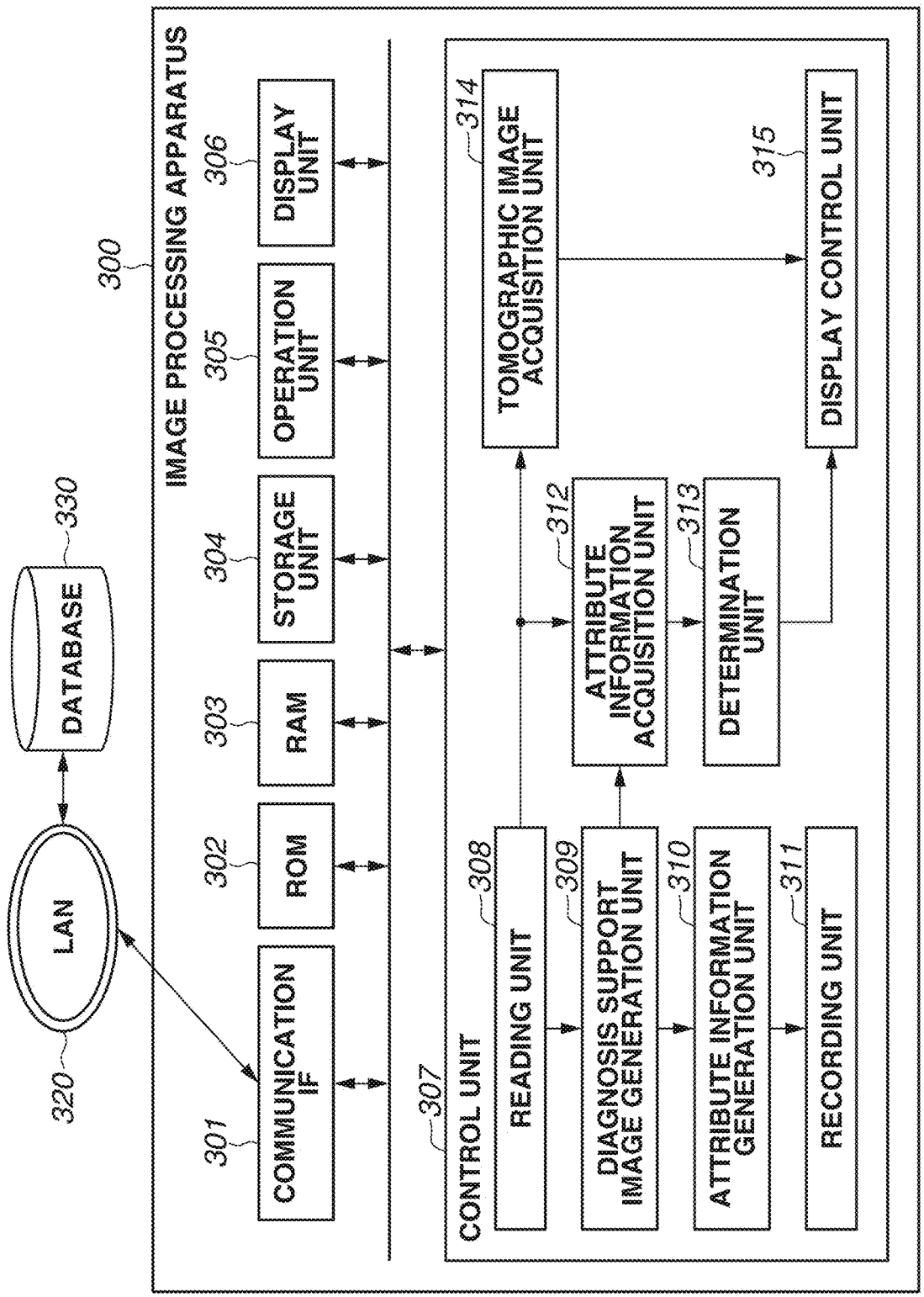
FIG. 3 is a block diagram illustrating an example of an overall configuration of an image processing system including an image processing apparatus according to a second exemplary embodiment.

FIG. 3 is a block diagram illustrating an overall configuration of an image processing system including an image processing apparatus according to the present exemplary embodiment. A configuration of the image processing system according to the present exemplary embodiment can be the same as or similar to that of the first exemplary embodiment. A control unit of the image processing apparatus has a different functional configuration, and thus a functional configuration thereof will be described below. Functional configurations of the rest of constituent elements can be the same as or similar to those of the first exemplary embodiment, so further description thereof will be omitted.

The image processing system includes an image processing apparatus 300 and a database 330, which are communicably connected to each other via a communication means 320. In the present exemplary embodiment, the communication means 320 is configured of a local area network (LAN).

The database 330 stores and manages data, such as a medical image. The image processing apparatus 300 acquires a medical image managed by the database 330 via the communication means (e.g., LAN) 320.

A control unit 307 includes, as a functional configuration, a reading unit 308, a diagnosis support image generation unit 309, an attribute information generation unit 310, a recording unit 311, an attribute information acquisition unit 312, a determination unit 313, a tomographic image acquisition unit 314, and a display control unit 315. Functions of respective units included in the control unit 307 will be described with reference to flowcharts in FIGS. 4 to 6.

Figure 4:
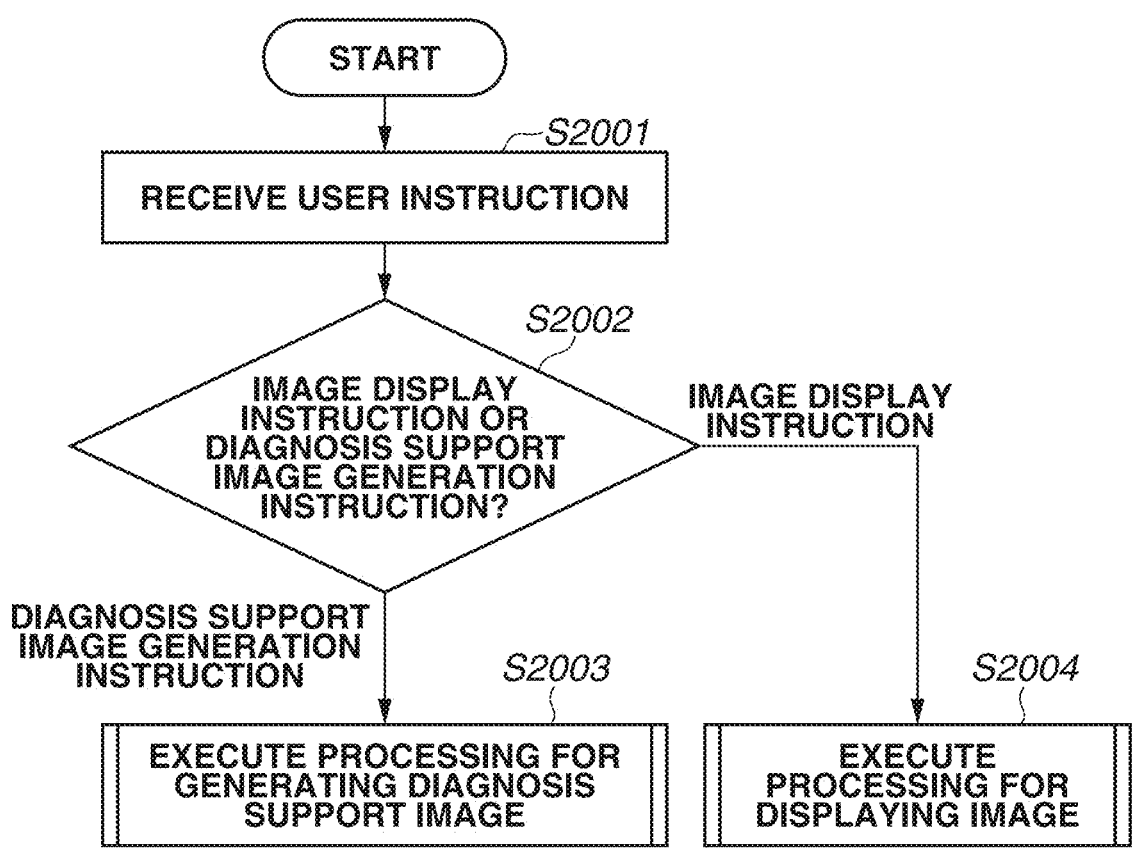
FIG. 4 is a flowchart illustrating an example of a first processing procedure according to the second exemplary embodiment.

A first processing procedure of the image processing apparatus 300 according to the present exemplary embodiment will be described with reference to the flowchart in FIG. 4.

<Receiving User Instruction>

In step S2001, the control unit 307 receives a user instruction input to the operation unit 305.

<Determining User Instruction>

In step S2002, the control unit 307 determines the processing to be executed next based on the user instruction input to the operation unit 305. If the user instruction is an instruction to generate a diagnosis support image ("DIAGNOSIS SUPPORT IMAGE GENERATION INSTRUCTION" in step S2002), the processing proceeds to step S2003. If the user instruction is an image display instruction ("IMAGE DISPLAY INSTRUCTION" in step S2002), the processing proceeds to step S2004. Although there are a wide variety of user instructions relating to control executed by the control unit 307, description of the other user instructions will be omitted to simply describe the disclosure of this specification.

<Processing for Generating Diagnosis Support Image>

Figure 5:
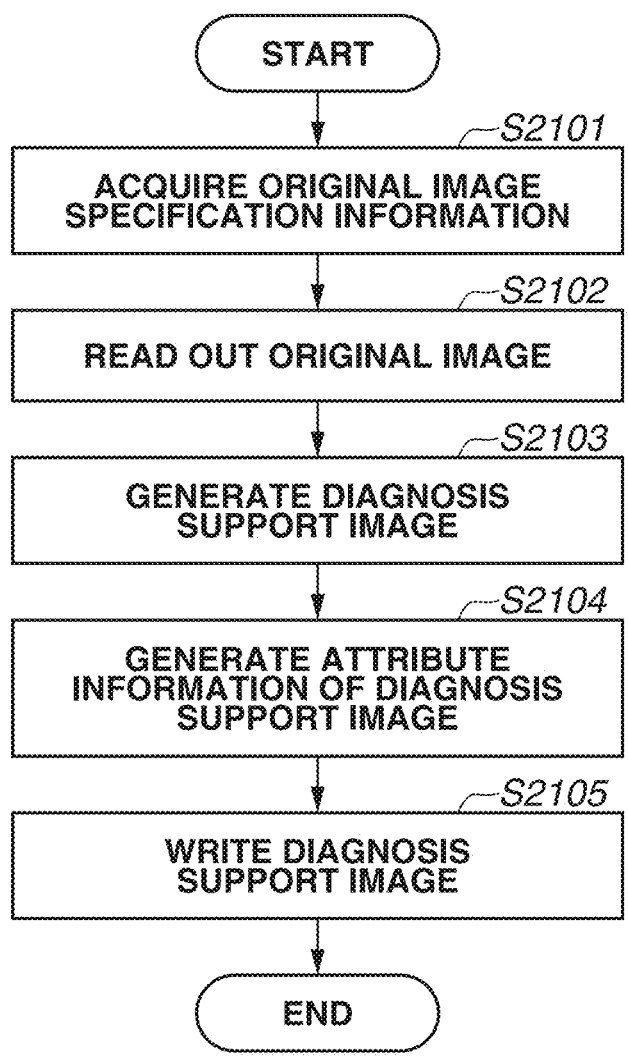
FIG. 5 is a flowchart illustrating an example of a second processing procedure according to the second exemplary embodiment.

In step S2003, the control unit 307 executes processing for generating the diagnosis support image described in FIG. 5, and ends the processing.

<Processing for Displaying Image>

Figure 6:
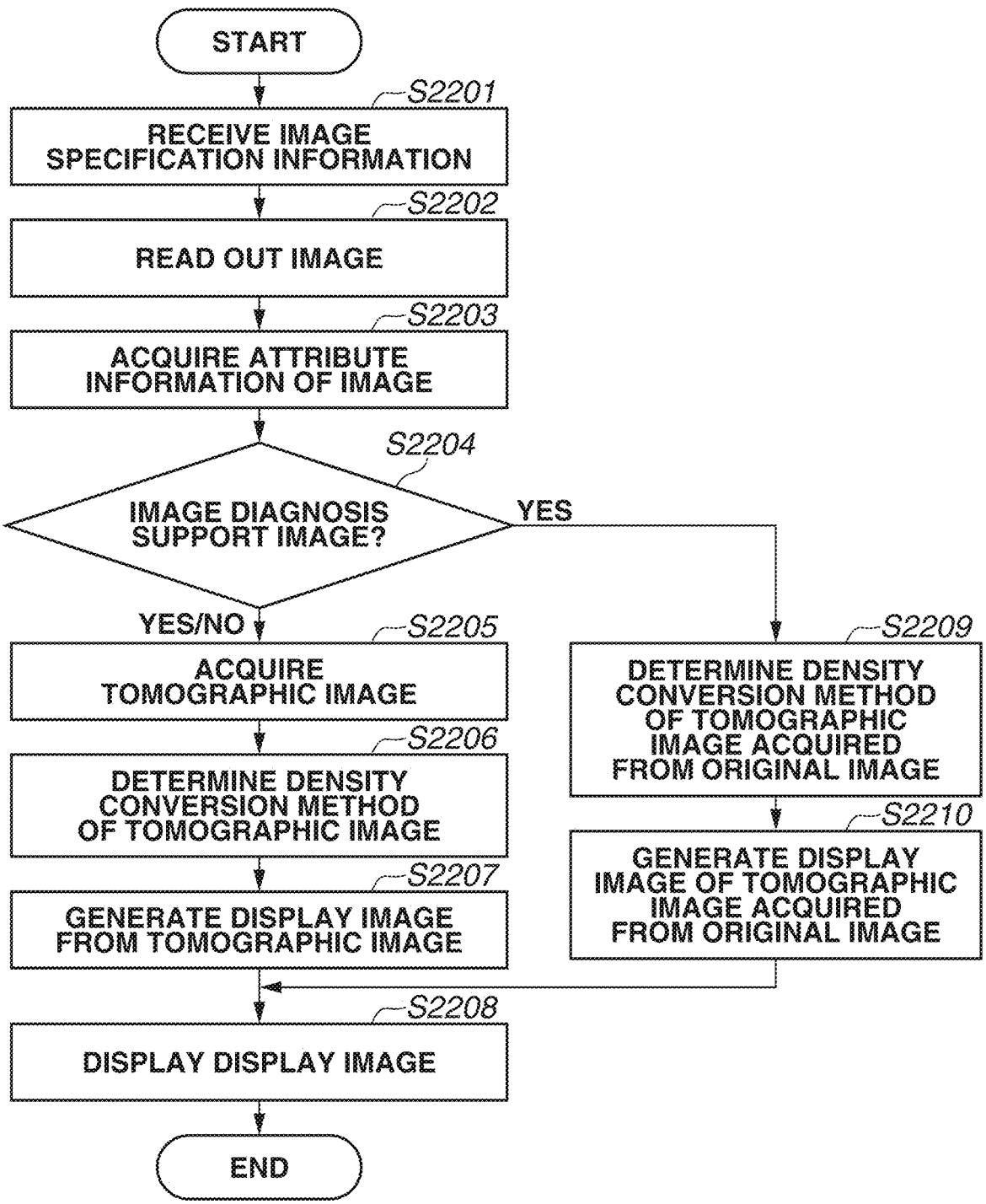
FIG. 6 is a flowchart illustrating an example of a third processing procedure according to the second exemplary embodiment.

In step S2004, the control unit 307 executes image processing described in FIG. 6, and ends the processing.

A second processing procedure performed by the image processing apparatus 300 according to the present exemplary embodiment will be described with reference to the flowchart in FIG. 5. Specifically, FIG. 5 is a flowchart illustrating details of the processing procedure (e.g., processing for displaying the diagnosis support image) executed in step S2003 in FIG. 4.

<Acquiring Original Image Specification Information>

In step S2101, the control unit 307 receives information (hereinafter, referred to as "original image specification information") for specifying one or more original images used for generating the diagnosis support image from the operation unit 305. Herein, the number of original images varies depending on the type of diagnosis support image to be generated. In order to specifically describe the present exemplary embodiment, a processing procedure using a subtraction image as a diagnosis support image will be described below as an example. The subtraction image is generated by calculating a difference between two original images after registration is adjusted between the two original images. Further, in the below-described processing procedure, two CT images acquired by capturing the same patient at two different time points are used as the original images. The CT images are three-dimensional images, and thus a subtraction image generated from the two CT images is also a three-dimensional image.

<Reading Out Original Image>

In step S2102, based on the original image specification information received in step S2101, the reading unit 308 reads out original image data (two pieces of CT image data) from the database 330 via the communication IF 301 and the LAN 320, and records the original image data in the storage unit 304. At this time, if a size of the RAM 303 is large enough, the read original image data may be stored in the RAM 303.

<Generating Diagnosis Support Image>

In step S2103, the diagnosis support image generation unit 309 generates a diagnosis support image from the original image data recorded in the storage unit 304 (or the RAM 303) by using a known technique. Specifically, the diagnosis support image generation unit 309 generates a subtraction image from the two pieces of CT image data by using a known image registration adjustment technique and a known subtraction technique. The diagnosis support image generation unit 309 further generates, as described in the first exemplary embodiment, information (e.g., diagnosis support region information or region information) which identifies that diagnosis of what region of the patient's body is supported by the generated diagnosis support image.

<Generating Attribute Information of Diagnosis Support Image>

In step S2104, the attribute information generation unit 310 acquires attribute information from the original image data recorded in the storage unit 304 (or the RAM 303), and further acquires the diagnosis support region information generated in step S2103. Then, the attribute information generation unit 310 generates attribute information of the diagnosis support image by using the attribute information and the diagnosis support region information acquired from the original image data. If the original images are DICOM images, attribute information of the image is written into the DICOM headers. Herein, of the two CT images regarded as the original images, the CT image captured at a later time point is specified as a diagnosis target image. In this case, patient information, such as a patient's name, and attribute information, such as an examination region, are acquired from a header of the DICOM image captured at a later time point. An examination date/time is acquired from each of the DICOM headers of the two CT images. The attribute information generation unit 310 uses the attribute information, which is acquired from the DICOM headers of the original images, as the attribute information of the diagnosis support image. The attribute information generation unit 310 further uses a predetermined DICOM tag to write the diagnosis support region information into the DICOM header.

<Writing Diagnosis Support Image>

In step S2105, the recording unit 311 records the diagnosis support image generated in step S2103 and the attribute information of the diagnosis support image generated in step S2104 in the storage unit 304 (or the RAM 303) in association with each other. If the diagnosis support image is a three-dimensional image and is also a DICOM image, each of tomographic images constituting the three-dimensional image is regarded as a DICOM (tomographic) image. In other words, each of the DICOM (tomographic) images includes a DICOM header including the attribute information of the diagnosis support image and image data corresponding to a single tomographic image of the diagnosis support image.

Hereinafter, the diagnosis support image stored in association with the attribute information of the diagnosis support image is simply referred to as "diagnosis support image" for the sake of simplicity. In step S2105, the recording unit 311 may further write the diagnosis support image into the database 330 via the communication IF 301 and the LAN 320.

Next, a third processing procedure of the image processing apparatus 300 according to the present exemplary embodiment will be described with reference to the flowchart in FIG. 6. FIG. 6 is a flowchart illustrating details of the processing procedure (i.e., processing for displaying images) executed in step S2004 in FIG. 4.

<Receiving Image Specification Information>

In step S2201, the control unit 307 receives information to specify an image to be displayed on the display unit 306 (hereinafter, referred to as "image specification information") input through the operation unit 305.

<Reading Out Image>

In step S2202, the reading unit 308 checks whether an image specified by the image specification information received in step S2201 (hereinafter, referred to as "specified image") has already been stored in the storage unit 304 (or the RAM 303). If the specified image has already been stored, it is not necessary to further execute the processing in step S2202. On the other hand, if the specified image has not been stored, the reading unit 308 reads out image data from the database 330 via the communication IF 301 and the LAN 320 based on the image specification information, and records the image data in the storage unit 304 (or the RAM 303).

<Acquiring Attribute Information of Image>

In step S2203, the attribute information acquisition unit 312 reads out the specified image from the storage unit 304 (or the RAM 303) and acquires attribute information of the image. If the specified image is a DICOM image, the attribute information acquisition unit 312 acquires the attribute information of the image from a DICOM header of the specified image.

<Determining Diagnosis Support Image>

In step S2204, the determination unit 313 checks the attribute information of the specified image and determines whether the specified image is the diagnosis support image. The determination unit 313 may determine whether the specified image is the diagnosis support image based on an image type, or based on existence of a DICOM tag indicating diagnosis support region information, which is different from a DICOM tag indicating an imaging region, in the attribute information of the specified image. In a case where a DICOM tag indicating diagnosis support region information is previously included in both of the original image and the diagnosis support image, the determination unit 313 may make a determination based on whether information indicating the diagnosis support region exists in the DICOM tag. The processing proceeds to step S2205 regardless of whether the specified image is the diagnosis support image (YES/NO in step S2204). If the specified image is the diagnosis support image (YES in step S2204), the processing proceeds to step S2209. The determination unit 313 determines whether the specified image is the diagnosis support image based on existence of the diagnosis support region information. The determination unit 313 records the diagnosis support region information in the RAM 303 when the diagnosis support region information exists, and records information indicating non-existence of the diagnosis support region information (hereinafter, referred to as "NULL information") in the RAM 303 when the diagnosis support region information does not exist.

The determination unit 313 may advances the processing to step S2209 after the processing in steps S2205 to S2208 is completed, or may concurrently advance the processing to steps S2209 and step S2205 if the processing can be executed concurrently.

<Acquiring Tomographic Image>

In step S2205, the control unit 307 determines whether the specified image is a three-dimensional image consisting of a plurality of tomographic images. If the specified image is a three-dimensional image, the control unit 307 acquires a tomographic image of a predetermined position (e.g., starting position). Alternatively, if the specified image is a three-dimensional image, the control unit 307 receives information to specify a position of the tomographic image (hereinafter, referred to as "tomographic position information") from the operation unit 305, and acquires a tomographic image specified by the received tomographic position information. On the other hand, if the specified image is a two-dimensional image, the control unit 307 acquires the two-dimensional image by taking the two-dimensional image itself as equivalent to the above-described tomographic image. Finally, the control unit 307 records, in the RAM 303, the tomographic image acquired through one of the above-described methods in association with the diagnosis support information (or NULL information) stored in the RAM 303 in step S2204.

<Determining Density Conversion Method of Tomographic Image>

In step S2206, the determination unit 313 acquires information for specifying a density conversion method of the specified image (hereinafter, referred to as "density conversion specification information") from the attribute information of the specified image, and records the density conversion specification information in the RAM 303 together with the identification information of the specified image. The determination unit 313 then determines a density conversion method of the tomographic image acquired in step S2205 based on the density conversion specification information. In a case where the specified image is a DICOM image, a WL value and a WW value included in the DICOM header are taken as the density conversion specification information, and the density conversion method is specified by a density conversion formula described in the DICOM standard. A table 1 describes an example of the identification information and the density conversion specification information (e.g., a WL value and a WW value) of the image when the specified image is a DICOM image. The identification information of the image may be, for example, a series instance unique identifier (UID) included in the DICOM header, or may be, for example, information indicating a saving destination of the tomographic image stored in the RAM 303 in step S2205.

TABLE 1

| Identification Information of Image | WL Value | WW Value |
|---|---|---|
| Identification Information of Image 1 | 40 | 450 |
| Identification Information of Image 2 | 60 | 400 |

<Generating Display Image from Tomographic Image>

In step S2207, the display control unit 315 generates an image to be displayed on the display unit 306 (hereinafter, referred to as "display image") based on the tomographic image acquired in step S2205 and the density conversion method of the tomographic image determined in step S2206. If the tomographic image is selected from DICOM images, a pixel value (e.g., 8-bit value) of the display image is calculated and acquired by assigning the WL value, the WW value, and a pixel value (e.g., 16-bit value) of the tomographic image to the density conversion formula described in the DICOM standard.

<Displaying Display Image>

In step S2208, the display control unit 315 displays the display image generated in step S2207 on the display unit 306.

The display control unit 315 also displays a display image of the tomographic image acquired from the original image, generated in below-described step S2210, on the display unit 306, so that the originally-displayed display image is replaced.

<Determining Density Conversion Method of Tomographic Image Acquired from Original Image>

In step S2209, the determination unit 313 acquires a data set including the diagnosis support region information (or NULL information) and the tomographic image stored in the RAM 303 in steps S2204 and S2205. This data set exists by the number corresponding to the number of display images already displayed. The determination unit 313 then takes out a tomographic image associated with the NULL information but not associated with the diagnosis support region information. Herein, all of the tomographic images associated with the NULL information is acquired from the original image. The determination unit 313 further determines a display mode of the tomographic image acquired from the original image based on the type of the original image (e.g., CT or MRI) and the diagnosis support region information of the diagnosis support image determined in step S2204. In the present exemplary embodiment, the display mode of the tomographic image determined based on the diagnosis support region information includes a display parameter of the tomographic image. In the present exemplary embodiment, a density conversion parameter of the tomographic image is determined as a specific example of the display parameter. The determination unit 313 acquires a type of the original image from the attribute information of the tomographic image. A density conversion method is determined with respect to the DICOM image by determining the density conversion specification information (i.e., the WL value and the WW value) as the density conversion parameter.

A table 2 describes an example of the density conversion specification information (e.g., the WL value and the WW value) previously defined with respect to the type of original image and the diagnosis support region information. By previously determining a WL value and a WW value suitable for observing each region as the values used for observing a corresponding region with respect to each of the image types and diagnosis support regions, the user can change a density value of each of the original images to a value suitable for observing the region by simply displaying the diagnosis support image. Accordingly, the user can save time and effort to reset the WL value and the WW value of each of the original images.

TABLE 2

| Type of Original Image | Diagnosis Support Region Information | WL Value | WW Value |
|---|---|---|---|
| CT | Bone | 500 | 2500 |
| CT | Soft Tissue | 35 | 350 |
| CT | Brain | 35 | 150 |
| CT | Lung Field | −600 | 1500 |

The control unit 307 may determine preprocessing that is to be executed on a tomographic image to be displayed, based on the diagnosis support region information. For example, content of the preprocessing suitable for observing a region is previously defined for each diagnosis support region, and a tomographic image is displayed after the specified preprocessing is executed based on the acquired diagnosis support region information. With this configuration, a display mode can be determined based on the diagnosis support region information. Smoothing processing for reducing noise is executed when the diagnosis support region information indicates, for example, "Bone", whereas the smoothing processing is not executed when the diagnosis support region information indicates another region.

<Generating Display Image of Tomographic Image Acquired from Original Image>

In step S2210, the display control unit 315 generates a display image of the tomographic image acquired from the original image based on the tomographic image of the original image recorded in the RAM 303 in step S2205 and the density conversion method of the tomographic image determined in step S2209.

A screen example of a display image generated through the above-described processing steps is displayed on the display unit 306 will be described with reference to FIGS. 7 and 8.

Figure 7:
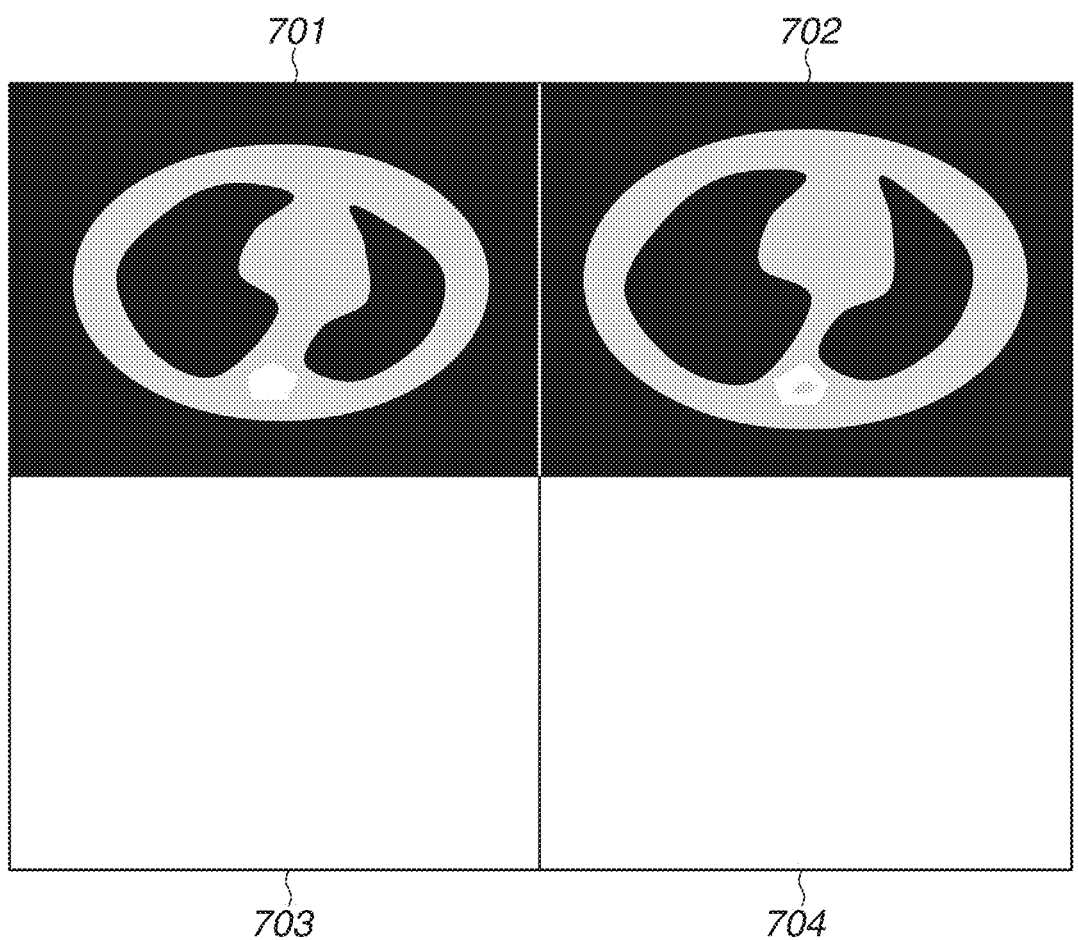
FIG. 7 is a diagram illustrating an example of a first screen displayed on a display unit of the image processing apparatus according to the second exemplary embodiment.

FIG. 7 is a diagram illustrating an example of a first screen displayed on the display unit 306 of the image processing apparatus 300 according to the present exemplary embodiment. Specifically, FIG. 7 illustrates an example of the screen to be displayed when a doctor as a user instructs the image processing apparatus 300 to display two original images (e.g., a CT image captured in the past and a CT image as a diagnosis target captured later). The screen as illustrated in FIG. 7 can be acquired by executing the processing performed in steps S2201 to S2208 in FIG. 6.

The number of original images displayed on the display unit 306 does not always have to be two, and one of the CT image captured in the past and the CT image as a diagnosis target captured later may be displayed on the display unit 306. In other words, the display control unit 315 corresponds to one example of a display control unit which displays at least one of the first image and the second image on a display unit.

In FIG. 7, a tomographic image acquired from the CT images captured in the past is displayed on an image display area 701. A tomographic image acquired from the CT image as a diagnosis target is displayed on an image display area 702. At this time, density conversion using, for example, the WL value and the WW value illustrated in the table 1 is executed on the display images displayed on the image display areas 701 and 702. These WL value and the WWW value are set by a doctor or a clinical radiologist according to the purpose of capturing a CT image. The CT image is used to show morphology (e.g., internal structure) of a patient' body, and can be applied to various medical examinations. Thus, there is a case where the CT image is observed for the purpose different from the purpose the CT image is captured for. Since one CT image may be observed for various purposes, the density is not always converted to be suitable for displaying a region which the doctor would like to observe even if the WL value and the WW value specified in the DICOM header are used. Therefore, a density conversion method conventionally has been specified newly according to a diagnostic purpose when the image is observed by the doctor.

Figure 8:
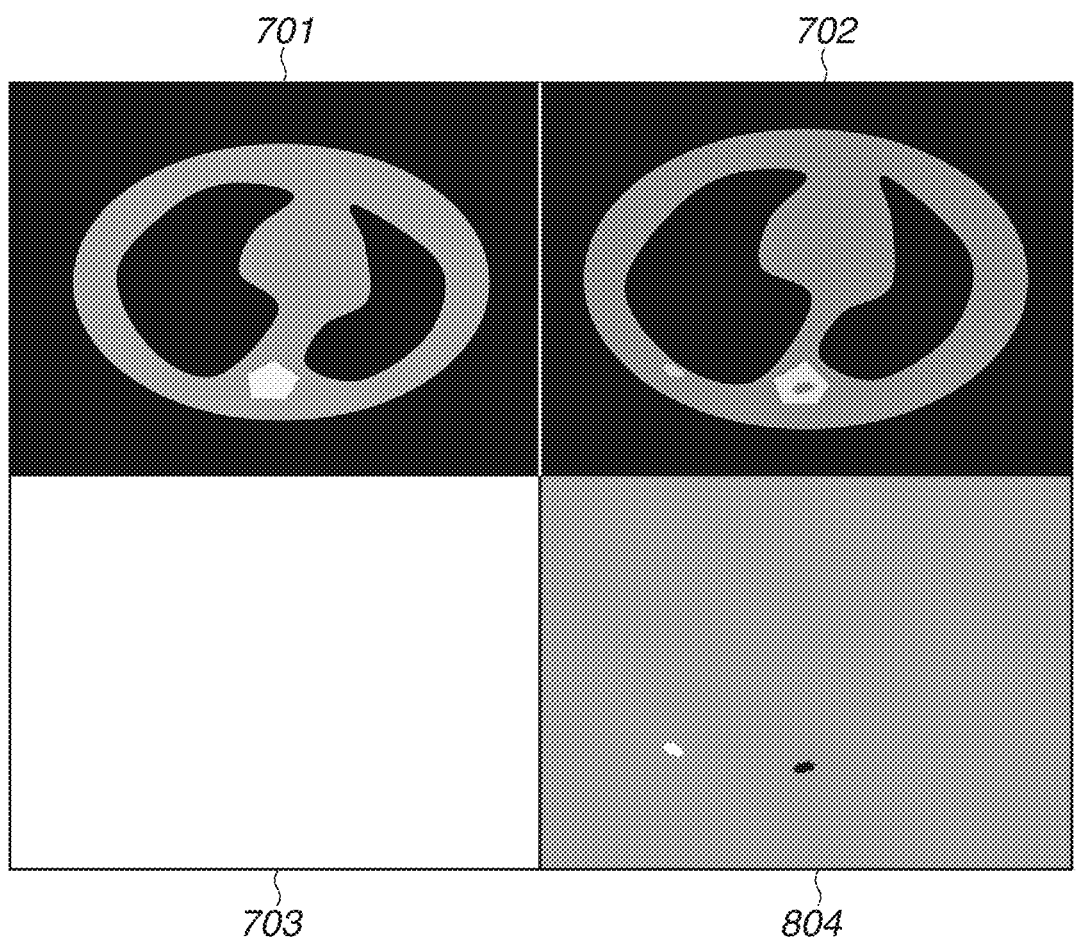
FIG. 8 is a diagram illustrating an example of a second screen displayed on the display unit of the image processing apparatus according to the second exemplary embodiment.

FIG. 8 is a diagram illustrating an example of a second screen displayed on the display unit 306 of the image processing apparatus 300 according to the present exemplary embodiment. The display unit 306 corresponds to one example of a display unit capable of displaying a first image, a second image, and a subtraction image. Specifically, FIG. 8 is a screen example illustrating a state where the doctor displays a diagnosis support image in addition to two original images. When the doctor thinks that it is difficult to make a diagnosis only based on the original images, the doctor can conduct observation by further adding the diagnosis support image to acquire diagnosis support information. Accordingly, quality of diagnosis can be improved. By executing all of the processing steps performed in FIG. 6, the screen example illustrated in FIG. 8 can be acquired.

In FIG. 8, in addition to the tomographic images acquired from two CT images, a tomographic image acquired from a subtraction image used as a diagnosis support image is displayed in an image display area 804. By executing the processing in steps S2201 to S2208 illustrated in FIG. 6, an image displayed in the image display area 804 can be acquired. By further executing the processing in steps S2209 to S2210, the display images displayed in the image display area 701 and 702 illustrated in FIG. 7 are changed to the images illustrated in FIG. 8. Herein, if the diagnosis support image is a subtraction image generated for the purpose of detecting the bone lesions, a WL value (500) and a WW value (2500) for "bones" illustrated in the table 2 are used in step S2209. Accordingly, the display images displayed in the image display areas 701 and 702 are displayed at the density suitable for observing bones. In other words, the display control unit 315 is an example of a display control unit that changes and displays display parameters of images other than a subtraction image displayed on a display unit based on information indicating a portion of a region commonly included in original images. Alternatively, the display control unit 315 corresponds to an example of a display control unit which changes a display parameter of an original image to a display parameter of a subtraction image to display the original image again in a case where the display parameter of the original image displayed on a display unit is different from the display parameter of the subtraction image.

According to the disclosure of the present specification described above, a density conversion method of the original image is determined based on the diagnosis support region information stored as the attribute information of the diagnosis support image, so that a display mode of the image can be determined without asking additional time and effort of the user. Since it is possible to make display parameters of the original image and the diagnosis support image conform to each other, visibility of lesions and quality of diagnosis can be improved.

Similar to the image processing apparatus according to the second exemplary embodiment, an image processing apparatus according to a third exemplary embodiment is an apparatus which displays a plurality of images, capable of setting (e.g., changing) one or more display modes of the images.

An image processing system including the image processing apparatus according to the present exemplary embodiment has an apparatus configuration can be the same as or similar to the apparatus configuration illustrated in FIG. 3, so further description of the apparatus configuration will be omitted. The first and the second processing procedures controlled by the control unit 307 of the image processing apparatus 300 according to the present exemplary embodiment can respectively be the same as or similar to the processing procedures illustrated in FIGS. 4 and 5. Thus, further description of the first and the second processing procedures performed in the present exemplary embodiment will be also omitted.

Figure 9:
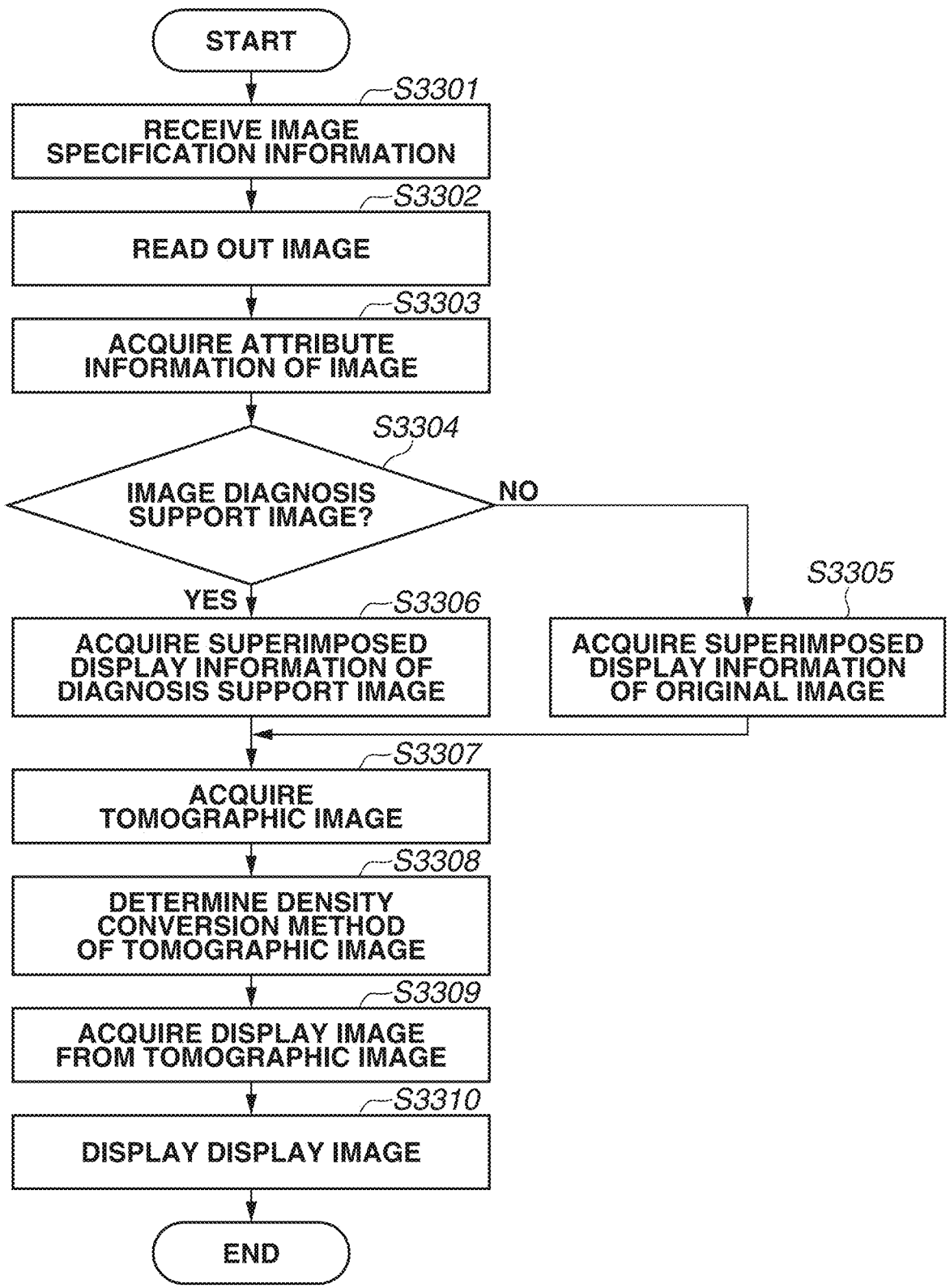
FIG. 9 is a flowchart illustrating an example of a third processing procedure according to a third exemplary embodiment.

A third processing procedure performed in the image processing apparatus 300 according to the present exemplary embodiment will be described with reference to the flowchart illustrated in FIG. 9. Specifically, the flowchart illustrates details of the processing procedure, i.e., the processing for displaying an image, executed in step S2004 illustrated in FIG. 4.

<Receiving Image Specification Information>

In step S3301, the control unit 307 receives information to specify an image to be displayed on the display unit 306 (hereinafter, referred to as "image specification information") input through the operation unit 305.

<Reading Out Image>

In step S3302, the reading unit 308 checks whether an image specified by the image specification information received in step S3301 (hereinafter referred to as "specified image") has already been stored in the storage unit 304 (or the RAM 303). If the specified image has already been stored, it is not necessary to further execute the processing in step S3302. On the other hand, if the specified image has not been stored, the reading unit 308 reads out image data from the database 330 via the communication IF 301 and the LAN 320 based on the image specification information, and records the image data in the storage unit 304 (or the RAM 303).

<Acquiring Attribute Information of Image>

In step S3303, the attribute information acquisition unit 312 reads out the specified image from the storage unit 304 (or the RAM 303) and acquires attribute information of the image. If the specified image is a DICOM image, the attribute information acquisition unit 312 acquires the attribute information of the image from a DICOM header of the specified image.

<Determining Diagnosis Support Image>

In step S3304, the determination unit 313 checks the attribute information of the specified image and determines whether the specified image is a diagnosis support image. If the specified image is not the diagnosis support image (NO in step S3304), the processing proceeds to step S3305. If the specified image is the diagnosis support image (YES in step S3304), the processing proceeds to step S3306. The determination unit 313 determines whether the specified image is the diagnosis support image depending on whether the diagnosis support region information exists in the attribute information of the specified image. The determination unit 313 records the diagnosis support region information in the RAM 303 when the diagnosis support region information exists. The determination unit 313 records information indicating non-existence of the diagnosis support region information (i.e., "NULL information") in the RAM 303 when the diagnosis support region information does not exist.

<Acquiring Superimposed Display Information of Original Image>

In step S3305, the determination unit 313 acquires information of the original image to be displayed on a screen (hereinafter, referred to as "display information of the original image") from the attribute information of the specified image. Display information of the original image includes patient information (e.g., a patient ID, a patient name, age, and sex), a modality (e.g., a type of image-capturing apparatus), and examination information (e.g., examination date/time and an examination region). The display information of the original image may be determined previously, or may be selected (changed) according to a user instruction received through the operation unit 305. Detailed description of a selecting method of the display information will be omitted. In step S3305, the determination unit 313 acquires information to be superimposed and displayed on a display area of the original image (hereinafter, referred to as "superimposed display information of the original image") by converting a display mode of the display information of the original image into a display mode to display the information on a screen of the display unit 306. Examples of the superimposed display information of the original image include display information of the original image converted into one or more rows of character strings and display information of the original image converted into one or more predetermined figures. Alternatively, a part of the display information of the original image may be converted into a character strings, whereas another part of the display information of the original image may be converted into a figure. In step S3305, the determination unit 313 further records the above-described superimposed display information of the original image in the RAM 303.

<Acquiring Superimposed Display Information of Diagnosis Support Image>

In step S3306, the determination unit 313 acquires information of the diagnosis support image to be displayed on a screen (hereinafter, referred to as "display information of the diagnosis support image") from the attribute information of the specified image. Although a part of the display information of the diagnosis support image is the same as the display information of the original image, diagnosis support region information (or NULL information) stored in the RAM 303 in step S3304 is acquired as unique information to the display information of the diagnosis support image. When the diagnosis support image is a subtraction image, display information of the original image acquired from two original images can be included in the display information of the subtraction image because two original images are used to acquire the subtraction image. For example, if the first and the second original images include different information (e.g., examination date/time), the two pieces of different information are displayed individually as the display information of the subtraction image. If the first and the second original images include common information (e.g., a patient name and an examination region), the information is displayed collectively. The display information of the diagnosis support image may be determined previously, or may be selected (changed) according to a user instruction received from the operation unit 305 (detailed description of a selecting method of the display information will be omitted). In step S3306, the determination unit 313 converts a display mode of the display information of the diagnosis support image into a display mode for displaying information on a screen of the display unit 306. Through this processing, information to be superimposed and displayed on a display area of the diagnosis support image (hereinafter, referred to as "superimposed display information of the diagnosis support image") is acquired. Similar to the superimposed display information of the original image, the superimposed display information of the diagnosis support image may be one or more rows of character strings, one or more figures, or a combination of the character strings and figures. In step S3306, the determination unit 313 further records the above-described superimposed display information of the diagnosis support image in the RAM 303.

<Acquiring Tomographic Image>

In step S3307, the control unit 307 determines whether the specified image is a three-dimensional image consisting of a plurality of tomographic images. If the specified image is a three-dimensional image, the control unit 307 acquires a tomographic image of a predetermined position (e.g., first position). Alternatively, the control unit 307 receives information for specifying a position of the tomographic image (hereinafter, referred to as "tomographic position information") through the operation unit 305, and acquires a tomographic image specified by the received tomographic position information. On the other hand, if the specified image is a two-dimensional image, the control unit 307 acquires the two-dimensional image by taking the two-dimensional image itself as equivalent to the above-described tomographic image. Finally, the control unit 307 records the tomographic image acquired through one of the above-described methods in the RAM 303 in association with the diagnosis support region information (or NULL information) stored in the RAM 303 in step S3304.

<Determining Density Conversion Method of Tomographic Image>

In step S3308, the determination unit 313 acquires information to specify a density conversion method of the specified image (hereinafter, referred to as "density conversion specification information") from the attribute information of the specified image. The determination unit 313 determines a density conversion method of the tomographic image acquired in step S3307 based on the density conversion specification information. In a case where the specified information is a DICOM image, the WL value and the WW value included in the DICOM header are acquired as the density conversion specification information, and the density conversion method is specified by a density conversion formula described in the DICOM standard.

<Acquiring Display Image from Tomographic Image>

In step S3309, the display control unit 315 acquires an image to be displayed on the display unit 306 (hereinafter, referred to as "display image") based on the tomographic image acquired in step S3307 and the density conversion method of the tomographic image determined in step S3308. If the tomographic image is selected from DICOM images, a pixel value (e.g., 8-bit value) of the display image is calculated and acquired by assigning the WL value, the WW value, and a pixel value (e.g., 16-bit value) of the tomographic image to the density conversion formula described in the DICOM standard.

<Displaying Display Image>

In step S3310, the display control unit 315 displays the display image generated in step S3309 on the display unit 306. The display control unit 315 superimposes and displays, on the display image, the superimposed display information of the original image or the diagnosis support image that has been stored in the RAM 303 in step S3305 or S3306. At this time, the display control unit 315 displays the superimposed display information based on the diagnosis support region information (or NULL information) determined and stored in the RAM 303 in step S3304. Specifically, the display control unit 315 displays the superimposed display information of the original image if diagnosis support region information is not stored in the RAM 303 (or the storage unit 304), and displays the superimposed display information of the diagnosis support image if diagnosis support region information is stored in the RAM 303 (or the storage unit 304).

Accordingly, the display control unit 315 performs as an example of a display control unit which superimposes and displays information indicating a diagnosis support region on a subtraction image. More specifically, the display control unit 315 performs as an example of a display control unit which superimposes and displays information indicating a portion (e.g., bone) of a region (e.g., abdominal region) commonly included in the original images on a subtraction image.

A screen example illustrating a state where the display image and the superimposed display image generated through the above-described processing steps are displayed on the display unit 306 will be described with reference to FIG. 10.

Figure 10:
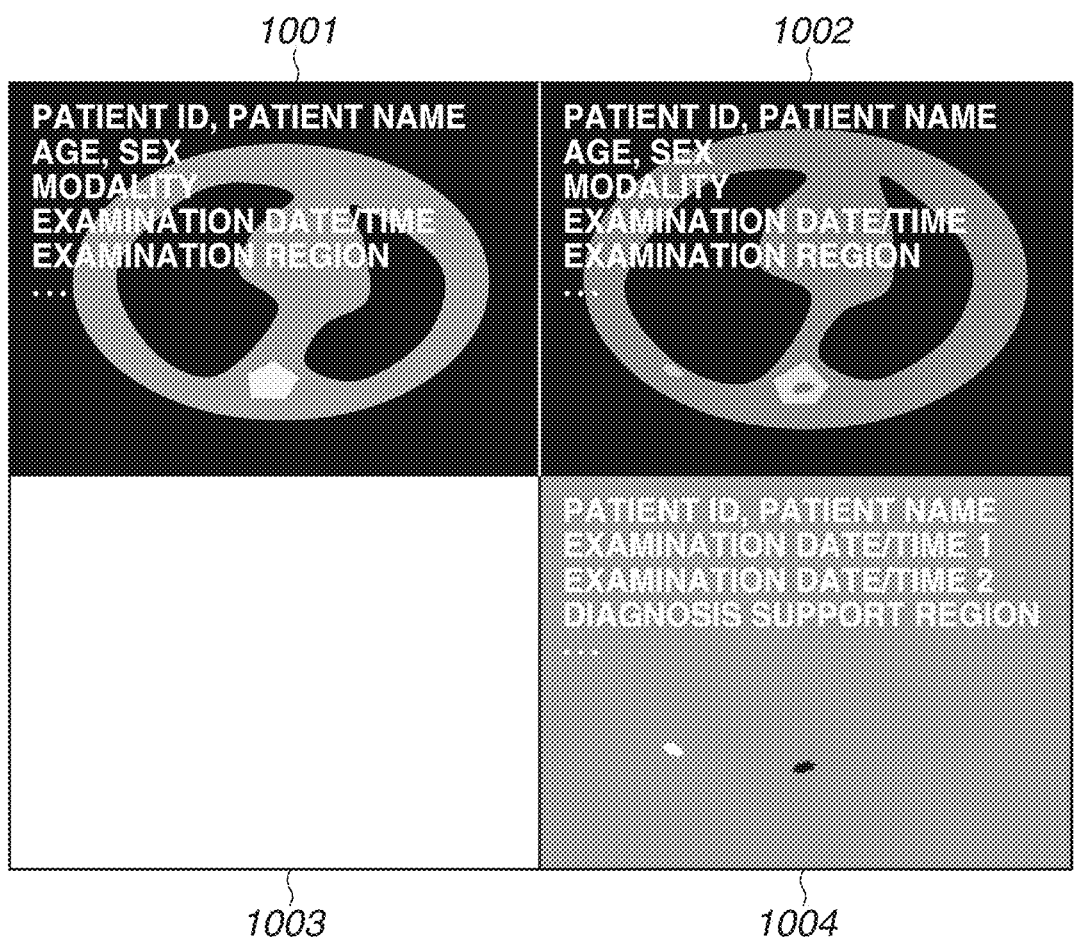
FIG. 10 is a diagram illustrating an example of a screen displayed on a display unit of the image processing apparatus according to the third exemplary embodiment.

FIG. 10 is a diagram illustrating an example of a screen displayed on the display unit 306 of the image processing apparatus 300 according to the present exemplary embodiment. Specifically, the screen example illustrates a state where the doctor displays a diagnosis support image in addition to two original images. When the doctor determines that it is difficult to make a diagnosis only based on the original images, the doctor can conduct observation by further adding the diagnosis support image to acquire diagnosis support information. Thus, quality of diagnosis can be improved. By executing all of the processing steps illustrated in FIG. 9, the screen example illustrated in FIG. 10 can be acquired.

In FIG. 10, a tomographic image acquired from a CT image captured in the past is displayed on an image display area 1001, and a tomographic image acquired from a CT image as a diagnosis target is displayed on an image display area 1002. A tomographic image acquired from a subtraction image as a diagnosis support image is displayed on an image display area 1004. Superimposed display information of the original image is further superimposed and displayed on the image display areas 1001 and 1002. Superimposed display information of the diagnosis support image is superimposed and displayed on the image display area 1004. As illustrated in FIG. 10, information indicating a diagnosis support region is displayed as the superimposed display information of the diagnosis support image. Thus, the user can easily recognize the diagnosis support region. The superimposed display information of the diagnosis support image illustrated in FIG. 10 includes the examination dates and times of the first and the second images. Since two examination dates and times are displayed on the first and the second images, the user can instantly recognize from which original images captured at two different time points the subtraction image regarded as a diagnosis support image is generated.

The above-described display method of attribute information is merely an example, and the display method is not limited thereto. For example, the diagnosis support region information may be displayed as a pop-up display when the user operates the operation unit 305 to adjust a cursor to a portion of the diagnosis support image representing a difference value, displayed on the image display area 1004. It is preferable that the pop-up display be displayed without overlapping with a portion where the difference value is displayed.

As described above, according to the disclosure of the specification, a display mode of the image can be determined automatically by generating the superimposed display information based on the diagnosis support region information (or NULL information) stored as the attribute information of the image. Further, by superimposing and displaying the superimposed display information on the image, a region emphasized in the diagnosis support image can easily be recognized when the user looks at the diagnosis support image, so that quality of diagnosis can be improved. According to the above-described exemplary embodiments, different information is superimposed and displayed on each of the original image and the diagnosis support image. Thus, after the user knows the region captured in the image from the information superimposed and displayed on the original images, the user can recognize a portion to be noticed in the region from the information superimposed and displayed on the diagnosis support image, accordingly. Therefore, it is possible to improve quality of diagnosis.

As described in the second and the third exemplary embodiments, a display mode of the image can be set without increasing the time and effort of the user even in a case where a plurality of images or a plurality of settable display modes exists, according to the disclosure of the specification.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-202866, filed Oct. 29, 2018, which is hereby incorporated by reference herein in its entirety.

What is claimed is:

1. An image processing apparatus that supports detection of pathological change over time in a portion of a captured region, the captured region common to a first image and a second image, the first image and the second image acquired by capturing a subject at different respective times, the image processing apparatus comprising:
a memory storing a program; and
one or more processors which, by executing the program, function as:
an acquisition unit configured to acquire a subtraction image of the first image and the second image representing the pathological change over time as a difference; and
a recording unit configured to record information to identify a region of the patient's body where diagnosis is supported by the subtraction image different from a name of the commonly included captured region in a storage unit in association with the subtraction image.

2. The image processing apparatus according to claim 1, wherein the information identifying the region is information that is not associated with the first image and the second image.

3. The image processing apparatus according to claim 1, wherein the acquisition unit acquires the subtraction image by generating the subtraction image from the first image and the second image.

4. The image processing apparatus according to claim 1, wherein the acquisition unit acquires the subtraction image by reading out the subtraction image recorded in the storage unit.

5. The image processing apparatus according to claim 1, wherein the one or more processors further functions as:
a display control unit configured to display at least one of the first image and the second image on a display unit; and
a determination unit configured to determine a display mode of an image to be displayed on the display unit based on the information identifying the region.

6. The image processing apparatus according to claim 5, wherein the display control unit displays an image that is or to be displayed on the display unit in a display mode determined by the determination unit.

7. The image processing apparatus according to claim 5, wherein the display control unit executes processing including at least one of smoothing processing and density conversion processing on an image to be displayed on the display unit.

8. The image processing apparatus according to claim 5, wherein the display control unit superimposes and displays information that is different from information superimposed and displayed on the first image and the second image by at least one item on the subtraction image.

9. The image processing apparatus according to claim 5, wherein the display control unit superimposes and displays information identifying the region on the subtraction image.

10. The image processing apparatus according to claim 5,
wherein the display control unit displays the information identifying the region on the subtraction image as a pop-up display, and
wherein the pop-up display is displayed without overlapping said portion.

11. The image processing apparatus according to claim 1,
wherein the commonly included captured region is a pectoral region, an abdominal region, a thoraco-abdominal region, or a cephalic region, and
wherein the identified region is a bone portion, a liver, a lung field, or a brain.

12. An image processing apparatus comprising:
a memory storing a program; and
one or more processors which, by executing the program, function as:
a display control unit configured to display a subtraction image and an original image of the subtraction image on a display unit,
wherein, the display control unit sets, as display parameters of the original image, display parameters based on a portion that supports detection of pathological change over time recorded in association with the subtraction image and displays the original image on the display unit.

13. An image processing method comprising:
displaying, through first display, a plurality of images on a display unit with a first display parameter; and
displaying, through second display, a subtraction image generated from the plurality of images on the display unit with a second display parameter,
wherein the second display includes processing to set, as display parameters of the plurality of images, display parameters based on a portion that supports detection of pathological change over time recorded in association with the subtraction image, and display the plurality of images.

14. An image processing method to support detection of pathological change over time in a portion of a captured region, the captured region common to a first image and a second image, the first image and the second image acquired by capturing a subject at different respective times, the image processing method comprising:
acquiring a subtraction image of the first image and the second image representing the pathological change over time as a difference; and
recording information to identify a region of the patient's body where diagnosis is supported by the subtraction image different from a name of the commonly included captured region in a storage unit in association with the subtraction image.

15. A non-transitory computer-readable storage medium storing a program for causing a computer to perform an image processing method to support detection of pathological change over time in a portion of a captured region, the captured region common to a first image and a second image, the first image and the second image acquired by capturing a subject at different respective times, the image processing method comprising:
acquiring a subtraction image of the first image and the second image representing the pathological change over time as a difference; and recording information to identify a region of the patient's body where diagnosis is supported by the subtraction image different from a name of the commonly included captured region in a storage unit in association with the subtraction image.

\* \* \* \* \*